US009452122B2

(12) United States Patent
Yang et al.

(10) Patent No.: US 9,452,122 B2
(45) Date of Patent: Sep. 27, 2016

(54) COMPOSITION FOR IMPROVING SKIN CONDITIONS, CONTAINING EXTRACELLULAR DOMAIN OF HUMAN BONE MORPHOGENETIC PROTEIN RECEPTOR 1A AS ACTIVE INGREDIENT

(75) Inventors: Zung Yoon Yang, Incheon (KR); Byung Hak Yoon, Incheon (KR); Seung-Hyon Choi, Gyeonggi-do (KR)

(73) Assignee: JOINT CENTER FOR BIOSCIENCES, Incheon (KR)

( * ) Notice: Subject to any disclaimer, the term of this patent is extended or adjusted under 35 U.S.C. 154(b) by 49 days.

(21) Appl. No.: 14/241,939

(22) PCT Filed: Aug. 30, 2012

(86) PCT No.: PCT/KR2012/006949
§ 371 (c)(1),
(2), (4) Date: Jun. 12, 2014

(87) PCT Pub. No.: WO2013/032248
PCT Pub. Date: Mar. 7, 2013

(65) Prior Publication Data

US 2014/0335155 A1 Nov. 13, 2014

(30) Foreign Application Priority Data

Aug. 31, 2011 (KR) ........................ 10-2011-0087615
Aug. 24, 2012 (KR) ........................ 10-2012-0092803

(51) Int. Cl.
*A61K 38/00* (2006.01)
*A61K 38/16* (2006.01)
*A61K 8/64* (2006.01)
(Continued)

(52) U.S. Cl.
CPC . *A61K 8/64* (2013.01); *A61K 8/14* (2013.01); *A61K 38/179* (2013.01); *A61Q 19/08* (2013.01); *C07K 14/71* (2013.01);
(Continued)

(58) Field of Classification Search
None
See application file for complete search history.

(56) References Cited

U.S. PATENT DOCUMENTS

2003/0215836 A1* 11/2003 Young et al. ..................... 435/6
2005/0152860 A1 7/2005 Yaar et al.
(Continued)

FOREIGN PATENT DOCUMENTS

KR 10-2010-0100708 A 9/2010
WO WO 2007/028212 A1 * 3/2007

OTHER PUBLICATIONS

Yoon et al., 2013, BMB Rep. 46(9):465-470.*
(Continued)

*Primary Examiner* — Elizabeth C Kemmerer
(74) *Attorney, Agent, or Firm* — Harness, Dickey & Pierce, P.L.C.

(57) ABSTRACT

The present invention provides a composition for improving skin conditions, containing the extracellular domain of human bone morphogenetic protein receptor 1a as an active ingredient. The present invention contains the extracellular domain of human bone morphogenetic protein receptor 1a as an active ingredient inside a nanoliposome comprising hydrogenated lecithin as a constituent component, and the particle size is 50-250 nm. The composition of the present invention reduces wrinkles and alleviates atopic dermatitis. In addition, the present invention provides a method for improving skin conditions, comprising the step of administering a composition containing the extracellular domain of human bone morphogenetic protein receptor 1a as an active ingredient to a subject.

11 Claims, 10 Drawing Sheets

UV(-)

UV(+)

UV + EtOH

UV + Retinoic acid

UV + Liposome

UV + Lipo-BMPR1a ECD

(51) Int. Cl.
*C07K 14/71* (2006.01)
*A61K 38/17* (2006.01)
*A61Q 19/08* (2006.01)
*A61K 8/14* (2006.01)

(52) U.S. Cl.
CPC .... *A61K 2800/412* (2013.01); *A61K 2800/74* (2013.01); *C07K 2319/00* (2013.01)

(56) References Cited

U.S. PATENT DOCUMENTS

2009/0263473 A1* 10/2009 Hong et al. .................. 424/450
2010/0266612 A1 10/2010 Seehra

OTHER PUBLICATIONS

Noda et al. (2015, J. Allergy Clin. Immunol. 135:324-336).*
Wittmann et al. (2014, Cytokine & Growth Factor Reviews 25:443-451).*
Allendorph, G.P. et al., "BMP-3 and BMP-6 Structures Illuminate the Nature of Binding Specificity with Receptors", Biochemistry, 2007, vol. 46, pp. 12238-12247. (See p. 12239.).
Botchkarev, V.A., "Bone morphogenetic proteins and their antagonists in skin and hair follicle biology", Journal of Investigative Dennato1ogy, 2003, vol. 120, pp. 36-47. (See pp. 41-44.).

* cited by examiner

TNCB (+)

TNCB (+)
DMSO

TNCB (+)
FK506

TNCB (+)
Liposome

TNCB (+)
Lipo-BMPRIa ECD

| UV irradiation | - | + | + | + | + |
|---|---|---|---|---|---|
| Sample | - | - | Retinoic Acid | Lipo-BMPR1a ECD | Lipo-thioredoxin -BMPR1a ECD |

COMPOSITION FOR IMPROVING SKIN CONDITIONS, CONTAINING EXTRACELLULAR DOMAIN OF HUMAN BONE MORPHOGENETIC PROTEIN RECEPTOR 1A AS ACTIVE INGREDIENT

CROSS REFERENCE TO RELATED APPLICATIONS AND CLAIM OF PRIORITY

This patent application is a National Phase application under 35 U.S.C. §371 of International Application No. PCT/KR2012/006949, filed 30 Aug. 2012, which claims priority to Korean Patent Application Nos. 10-2011-0087615, filed 31 Aug. 2011 and 10-2012-0092803, filed 24 Aug. 2012, entire contents of which are incorporated herein by reference.

TECHNICAL FIELD

The present invention relates to a composition for improving skin conditions, containing an extracellular domain of human bone morphogenetic protein receptor 1a as an active ingredient.

BACKGROUND ART

Bone morphogenetic proteins (BMPs) are multifunctional growth factors that are members of the transforming growth factor β (TGFβ) superfamily. BMP signaling plays a role in heart, neural, and cartilage development as well as in postnatal bone formation. BMPs induce a cascade of endochondral bone formation and play a decisive role in skeletal and joint morphogenesis (Urist, *Science,* 150:893-899 (1965), Olsen et al., *Annu. Rev. Cell Dev. Biol.* 16:191-220 (2000), Kronenberg, *Nature* 423:332-336 (2003), Thomas et al., *Nat. Genet.* 12:315-317 (1996), Thomas et al., *Nat. Genet.* 17:58-64 (1997), Polinkowsky et al., *Nat. Genet.* 17:18-19 (1997), Storm et al., *Nature,* 368:639-643 (1994)).

BMPs signal through serine/threonine kinase receptors including both types 1 and 2. Three type 1 receptors [type 1a and 1b BMP receptors and type 1 activin receptor (ActRI)] bind to BMP ligands (Koenig et al., *Mol. Cell. Biol.* 14:5961-5974 (1994), Ten Dijke et al., *J. Biol Chem.* 269: 16985-16988 (1994), Macias-Silva et al., *J. Biol. Chem.* 273:25628-25636 (1998)).

BMPs are synthesized as large dimeric precursor-proteins in the cytoplasm, and cleaved by proteases during secretion. Each monomer contains about 300 amino acids as the precursor proteins. The functional carboxy region (100-120 amino acids in each monomer) is released into the extracellular compartment to bind membrane receptors on target cells. There are a series of extracellular proteins that antagonize or otherwise alter the function of BMPs; these proteins include Glypican-3, Noggin, Chordin, Cerberus, and Follistatin (Fainsod et al., *Mech. Dev.* 63:39-50 (1997), Grisaru et al., *Dev. Biol.* 231:31-46 (2001), Holley et al., *Cell* 86:607-617 (1996), Iemura et al., *Proc. Natl. Acad. U.S.A.* 95:9337-9342 (1998), Jackson et al., *Development* 124: 4113-4120 (1997), Paine-Saunders et al., *Dev. Biol.* 225: 179-187 (2000), Piccolo et al., *Cell* 86:589-598 (1996), Re'em-Kalma et al., *Proc. Natl. Acad. Sci. U.S.A.* 92:12141-12145 (1995), Sasai et al., *Nature* 376:333-336 (1995), Zimmerman et al., *Cell* 86:599-606 (1996)). Type I and II BMP receptors are differentially expressed in various tissues, but both are indispensable for signal transduction. At the time of ligand binding, the type 1 and 2 BMP receptors form heterotetrameric-activated receptor complexes, which include two pairs of type 1 and 2 receptor complexes (Moustakas et al., *Genes Dev.* 16:67-87 (2002). Both receptor types are essential for signal transduction (Hogan, *Genes Dev.* 10:1580-1594 (1996), Nellen et al., *Cell* 78:225-237 (1994), Ruberte et al., *Cell* 80:889-897 (1995), Ten Dijke et al., *Curr. Opin. Cell Biol.* 8:139-145 (1996), Weis-Garcia et al., *EMBO J.* 15:276-289 (1996), Wrana et al., *Nature* 370:341-347 (1994)). Type 2 receptors have constitutively active kinase activity to phosphorylate type 1 receptors at the time of ligand binding. Phosphorylated type 1 receptors signal to downstream target proteins.

Type I BMP receptors signal through Smad proteins (Smad 1/5), which are important in relaying the BMP signal from the receptors to the target genes in the nucleus. When being released from the receptor, the phosphorylated Smad proteins associate with the related protein Smad4, which acts as a shared partner. This complex enters the nucleus, and participates in gene transcription with other transcription factors.

It has been little known that type 1 BMP receptor proteins, which play an important role in signaling, have improvement effects in wrinkles and atopic dermatitis.

Wrinkles are formed by the repeated movement of muscles in a particular direction for a long time, and are influenced by age, external environment, UV radiation, and the like. That is, human skin fibroblasts in the dermis layer are aged with the age of the skin tissue, so that the ability to generate fibers and substrates is reduced. Therefore, the amount of substrates is generally decreased, and thus the skin becomes thinned and inelastic, leading to the formation of wrinkles. Moreover, the exposure of the skin to UV radiation results in free radicals and reactive oxygen species (ROS), which are mainly causative of the damage of skin cells. These may generate age spots by inducing DNA damage and attacking the cell membrane structure, and accelerate wrinkle formation by attacking collagen and fibers which keep the skin to be moist, smooth, flexible, and elastic. Various methods for reducing skin wrinkles that are formed due to the external environment or internal mechanism have been supposed.

Meanwhile, atopy refers to an innate allergic reaction to food or other inhalable materials, but most of atopic diseases are intractable diseases of which causes are not clear Atopic dermatitis occurs in people who have an inherited predisposition to eczema, asthma, hay fever, allergy, and the like in many cases, but more causes thereof are known to be environmental factors such as residential pollution in modern cities. Atopic dermatitis is a chronic skin disease that tends to be chronic and recurrent starting from infant eczema called congenital fever.

Atopic dermatitis occurs in 10-20% of children and 1-3% of adults. According to the age, the symptoms thereof start from under one year old for 60% of infant patients and under five years old for 90% of infant patients. It is estimated that 4% of Korea's total population (about 185 million people) have atopic symptoms. The number of people with atopic symptoms is still increasing, which can be verified from recent research that four out of ten children under 6 years old living in Seoul suffered from atopic dermatitis (as reported by the Dong-A Ilbo on Dec. 27, 2005).

Symptoms of atopic dermatitis in infants are much improved by about 3-5 years old, but some cases continue until adolescence or adulthood. In recent years, the onset of atopic patients even after adolescence is increasing. For atopic dermatitis treatment, there are: a skin care method, in other words, softening the dry, cracked, and thickened skin to prevent the easy penetration of causative allergens, microorganisms, and other stimulating factors into the skin; a method of checking and removing accurate allergic causatives; a method of applying topical anti-inflammatory drugs and antibiotics; and the like.

Throughout the entire specification, many papers and patent documents are referenced and their citations are represented. The disclosures of cited papers and patent documents are entirely incorporated by reference into the present specification, and the level of the technical field within which the present invention falls and details of the present invention are explained more clearly.

DETAILED DESCRIPTION OF THE INVENTION

Technical Problem

The present inventors have endeavored to develop materials capable of improving skin conditions. As a result, the present inventors have found that the topical application of human bone morphogenetic protein receptor 1a extracellular domain (BMPR1a ECD) can significantly improve skin conditions, and then completed the present invention.

Accordingly, an objective of the present invention is to provide a composition for improving skin conditions, containing, as an active ingredient, a protein having the amino acid sequence of SEQ ID NO: 1.

Other objects and advantages of the present invention will become apparent from the following detailed description together with the appended claims and drawings.

Technical Solution

In accordance with an aspect of the present invention, there is provided a composition for improving skin conditions, the composition including a protein having the amino acid sequence of SEQ ID NO: 1 as an active ingredient.

The present inventors have researched and endeavored to find out novel uses of human bone morphogenetic protein receptor 1a extracellular domain (BMPR1a ECD). As a result, the present inventors have found that the topical application of an extracellular domain of human bone morphogenetic protein receptor 1a can significantly improve skin conditions.

The human bone morphogenetic protein receptor 1a extracellular domain (BMPR1a ECD) used as an active ingredient in the present invention constitutes a human bone morphogenetic protein receptor together with a single transmembrane domain and an intracellular kinase domain.

The human bone morphogenetic protein receptor 1a extracellular domain in the present application includes the amino acid sequence of SEQ ID NO: 1. The nucleic acid molecule encoding the human bone morphogenetic protein receptor 1a extracellular domain in the present application includes most preferably the nucleotide sequence of SEQ ID NO:2. The nucleic acid molecule encoding the human bone morphogenetic protein receptor 1a extracellular domain includes nucleotide sequences substantially identical to the above-described nucleotide sequence. The substantial identity means that, when a nucleotide sequence is aligned to maximally match the nucleotide sequence of the present disclosure and the alignment is analyzed using an algorithm commonly used in the art, it has an identity of at least 80%, more preferably at least 90%, and most preferably at least 95%.

The present invention provides a human bone morphogenetic protein receptor 1a extracellular domain (BMPR1a ECD) expressing vector containing the foregoing nucleic acid molecule encoding human bone morphogenetic protein receptor 1a extracellular domain (BMPR1a ECD).

The vector system of this invention may be performed by various methods known to those skilled in the art and its practical method is described in Sambrook et al., Molecular Cloning, A Laboratory Manual, Cold Spring Harbor Laboratory Press (2001), which is herein incorporated by reference.

Typically, the vector of this invention may be constructed as cloning or expression vector. In addition, the vector of this invention may be constructed using a prokaryotic or eukaryotic cell as a host cell.

For instance, it is common to include a strong promoter for transcription (e.g., tac promoter, lac promoter, lac UV5 promoter, lpp promoter, $p_L^{\lambda}$ promoter, $p_R^{\lambda}$ promoter, rac5 promoter, amp promoter, recA promoter, SP6 promoter, trp promoter and T7 promoter, and so on), a ribosomal binding site for translation initiation, and a transcription/translation termination sequence where each a vector of this invention and a prokaryotic cell is used in an expression vector and the host cell. *E. coli* (e.g., HB101, BL21, DH5α, etc.) as a host cell may utilize a promoter and operator region for tryptophan biosynthesis pathway (Yanofsky, C., *J. Bacteriol.,* 158:1018-1024 (1984)), and $p_L^{\lambda}$ promoter (Herskowitz, I. and Hagen, D., *Ann. Rev. Genet.,* 14:399-445 (1980)) as a regulatory region.

On the other hand, the suitable vector used in this invention might be constructed by manipulating a plasmid (example: pSC101, ColE1, pBR322, pUC8/9, pHC79, pUC19, pET and so on), or a virus (example: SV40) commonly used by one ordinarily skilled in the art.

In each a vector of this invention and an eukaryotic cell used as an expression vector and the host cell, the promoter derived from genome of animal cell (example: methallothionein promoter, β-actin promoter, human hemoglobin promoter and human muscle creatine promoter) or mammalian virus (example: adenovirus late promoter, vaccinia virus 7.5K promoter, SV40 promoter, cytomegalovirus promoter and tk promoter of HSV) might be used, and polyadenylated sequence might be commonly used as the transcription termination sequence.

The vector of this invention could be fused with other sequences to purify a protein of human bone morphogenetic protein receptor 1a extracellular domain expressed from it. For example, a fused sequence includes, but not limited to, glutathione-S-transferase (Pharmacia, USA), maltose-binding protein (NEB, USA), FLAG (IBI, USA) and 6×His (hexahistidine; Quiagen, USA) and so on.

The vector of the present invention used to purify human bone morphogenetic protein receptor 1a extracellular domain (BMPR1a ECD) may further contain a thioredoxin gene besides a human bone morphogenetic protein receptor 1a extracellular domain (BMPR1a ECD) gene.

On the other hand, the expression vector of this invention includes an antibiotics-resistance gene known to those ordinarily skilled in the art as a selection marker, for example resistant genes against ampicillin, gentamycin, carbenicillin, chloramphenicol, streptomycin, kanamycin, geneticin, neomycin and tetracycline.

In still another aspect of this invention, there is provided a host cell transformed with the above-described recombinant vector.

The host cells in which the present vector is stably and successively cloned and expressed, also utilize any one known to those skilled in the art, for example, *E. coli* JM109, *E. coli* BL21(DE3), *E. coli* RR1, *E. coli* LE392, *E. coli* B,

*E. coli*×1776, *E. coli* W3110, *Bacillus subtilis, Bacillus thuringiensis*, etc., and intestinal bacteria and strains including *Salmonella typhimurium, Serratia marcescens* and various *Pseudomonas* sp, preferably starpLys S *E. coli.*

In addition, mammalian-derived cells might be used as the host cells. Preferably, the host cells include, but not limited to, yeast (*Saccharomyce cerevisiae*), insect cell and human cell (e.g., CHO (Chinese hamster ovary) cell, W138, BHK cell, COS-7, 293, HepG2, 3T3, RIN and MDCK cell) and so on.

Delivery of the vector of the present disclosure into the host cell can be carried out by the $CaCl_2$ method (Cohen, S. N. et al., *Proc. Natl. Acac. Sci. USA,* 9: 2110-2114 (1973)), the Hannahan's method (Cohen, S. N. et al., *Proc. Natl. Acac. Sci. USA,* 9: 2110-2114 (1973); Hanahan, D., *J. Mol. Biol.,* 166: 557-580 (1983)), the electroporation method (Dower, W. J. et al., *Nucleic. Acids Res.,* 16: 6127-6145 (1988)), and the like.

The transformation of a host cell can be carried out by a large number of methods known to one skilled in the art. For example, in case of using prokaryotic cells as host, $CaCl_2$ method (Cohen, S. N. et al., *Proc. Natl. Acac. Sci. USA,* 9:2110-2114 (1973)), Hanahan method (Cohen, S. N. et al., *Proc. Natl. Acac. Sci. USA,* 9:2110-2114 (1973); and Hanahan, D., *J. Mol. Biol.,* 166:557-580 (1983)) and electrophoresis (Dower, W. J. et al., *Nucleic. Acids Res.,* 16:6127-6145 (1988)) can be used for transformation. Also, in case of using eukaryotic cells as host, microinjection (Capecchi, M. R., *Cell,* 22:479 (1980)), calcium phosphate precipitation (Graham, F. L. et al., *Virology,* 52:456 (1973)), electrophoresis (Neumann, E. et al., *EMBO J.,* 1:841 (1982)), liposome-mediated transfection (Wong, T. K. et al., *Gene,* 10:87 (1980)), DEAE-dextran treatment (Gopal, *Mol. Cell Biol.,* 5:1188-1190 (1985)), and particle bombardment (Yang et al., *Proc. Natl. Acad. Sci.,* 87:9568-9572 (1990)) can be use for transformation.

Vectors transfected to host cells that can be expressed in the host cells, in which a large quantity of the human bone morphogenetic protein receptor 1a extracellular domain proteins will be obtained. For example, if expression vector carries lac promoter, the induction of expression can be performed using IPTG (isopropyl-β-D-thiogalactopyranoside).

According to a preferable embodiment of the present invention, the composition of the present invention has a liposome. That is, human bone morphogenetic protein receptor 1a extracellular domain (BMPR1a ECD) as an active ingredient is preferably encapsulated in a liposome, and then applied to the skin. According to a more preferable embodiment of the present invention, the composition of the present invention has a nanoliposome. As used herein, the term "nanoliposome" refers to a liposome having a form of conventional liposome and a mean particle diameter of 20-1000 nm. According to a preferred embodiment of the present invention, the mean particle diameter of the nanoliposome is 50-500 nm, more preferably 50-350 nm, and most preferably 100-200 nm.

A liposome is defined as a spherical phospholipid vesicle of colloidal particles which are associated with themselves. The liposome composed of amphiphilic molecules each having a water soluble head (hydrophilic group) and a water insoluble tail (hydrophobic group) shows a structure aligned by spontaneous binding caused by the interaction therebetween. Liposomes are classified into small unilamellar vesicles (SUV), large unilamellar vesicles (LUV), and multi lamellar vesicles (MLV) according to the size and lamellarity thereof. The liposome showing various lamellarities as described above has a double membrane structure similar to that of the cell membrane.

The (nano)liposome in the present invention may be prepared by using phospholipid, polyol, a surfactant, fatty acid, and/or water.

The phospholipid which is a component used in the preparation of the (nano)liposome of the present invention is used as amphiphilic lipid. Examples thereof include natural phospholipids (e.g., egg yolk lecithin, soybean lecithin, and sphingomyelin) and synthetic phospholipids (e.g., dipalmitoylphosphatidylcholine or hydrogenated lecithin), and a preferable example thereof is lecithin. More preferably, the lecithin is hydrogenated lecithin derived from soybean.

The polyol which may be used in the preparation of the (nano)liposome of the present invention are not particularly limited, but examples thereof preferably include propylene glycol, dipropylene glycol, 1,3-butylene glycol, glycerin, methyl propanediol, isoprene glycol, pentylene glycol, erythritol, xylitol, and sorbitol.

The surfactant which may be used in the preparation of the (nano)liposome of the present invention may be any one known in the art, and examples thereof include anionic surfactants (e.g., alkyl acyl glutamate, alkyl phosphate, alkyl lactate, dialkyl phosphate, and trialkyl phosphate), cationic surfactants, amphoteric surfactants, and nonionic surfactants (e.g., alkoxylated alkylether, alkoxylated alkylester, alkylpolyglycoside, polyglycerylester and sugar ester).

The fatty acid which may be used in the preparation of the (nano)liposome of the present invention is higher fatty acid, and preferable examples thereof include saturated or unsaturated alkyl chain fatty acids having 12 to 22 carbon atoms, for example, lauric acid, myristic acid, palmitic acid, stearic acid, oleic acid, and linoleic acid.

The water which may be used in the preparation of the (nano)liposome of the present invention is generally deionized distilled water.

According to a preferred embodiment of the present invention, the (nano)liposome of the present invention is prepared by using only phospholipid and water, and a specific example thereof is described in the following example.

According to a preferred embodiment of the present invention, a human bone morphogenetic protein receptor 1a extracellular domain (BMPR1a ECD)-containing nanoliposome of the present invention is prepared by a process including: (a) dissolving phospholipid capable of forming liposome (preferably, hydrogenated lecithin) in an aqueous solution containing human bone morphogenetic protein receptor 1a extracellular domain (BMPR1a ECD); and (b) repeatedly passing the aqueous solution containing human bone morphogenetic protein receptor 1a extracellular domain (BMPR1a ECD) and the phospholipid through a high-pressure homogenizer, to prepare a nanoliposome containing human bone morphogenetic protein receptor 1a extracellular domain (BMPR1a ECD).

According to a preferable embodiment of the present invention, the nanoliposome of the present invention contains, as a main component, hydrogenated lecithin derived from soybean.

The aqueous solution containing human bone morphogenetic protein receptor 1a extracellular domain (BMPR1a ECD) is preferably a buffer solution of pH 6-8, and preferably about pH 7 (e.g., sodium phosphate buffer solution). If the sodium phosphate buffer solution is used, the concentration thereof is preferably 5-100 mM, more preferably 5-60 mM, still more preferably 10-30 mM, and most preferably about 20 mM.

Through the high-pressure homogenization process, human bone morphogenetic protein receptor 1a extracellular domain (BMPR1a ECD)-containing nanoliposome is prepared. Preferably, a liquid phase human bone morphogenetic protein receptor 1a extracellular domain (BMPR1a ECD)-containing nanoliposome is prepared.

The composition of the present invention may be used in improving various skin conditions. Preferably, the composition of the present invention is effective in wrinkle improvement, dermatitis diseases improvement, skin whitening, skin elasticity improvement, hair growth, anti-aging of skin, and improvement in skin moisturizing, and more preferably wrinkle improvement, epidermal thickness improvement, and atopic dermatitis improvement.

Dermatitis refers to eczematous dermatitis. Eczema is characterized by manifesting vesicle, erythema, and edema, accompanying itching at an acute period, and inducing lichniscation, scale, and skin color change while reducing edema and vesicle at a chronic period. Dermatitis diseases are classified into contact dermatitis, atopic dermatitis, and seborrheic dermatitis.

As used herein, the term "epidermal thickness improvement" refers to suppressing the thickening of skin epidermis.

The present composition may be prepared as a cosmetic or pharmaceutical composition.

The cosmetic compositions of this invention may contain ingredients usually used in cosmetic compositions, for example, including usual auxiliaries such as stabilizers, solubilizers, vitamins, colorants and odor improvers and carriers, as well as a human bone morphogenetic protein receptor 1a extracellular domain (BMPR1a ECD)-containing nanoliposome as active ingredients.

The cosmetic compositions for skin protection of this invention may be formulated in a wide variety of forms, for example, including a solution, a suspension, an emulsion, a paste, an ointment, a gel, a cream, a lotion, a powder, soap, a surfactant-containing cleanser, an oil, a powder foundation, an emulsion foundation, a wax foundation and a spray. Specifically, the cosmetic compositions of this invention may be formulated in the form of skin softener, nutrient liquid, nutrient cream, massage cream, essence, eye cream, cleansing cream, cleansing foam, cleansing water, pack, spray or powder.

Where the cosmetic composition is in the form of paste, cream or gel, it may comprise animal and vegetable fats, waxes, paraffins, starch, tragacanth, cellulose derivatives, polyethylene glycols, silicones, bentonites, silica, talc or zinc oxide.

In the formulation of powder or spray, it may comprise lactose, talc, silica, aluminum hydroxide, calcium silicate or polyamide powder. Spray may additionally comprise the customary propellants, for example, chlorofluorohydrocarbons, propane/butane or dimethyl ether.

The formulation of solution and emulsion may comprise solvent, solubilizer and emulsifier, for example water, ethanol, isopropanol, ethyl carbonate, ethyl acetate, benzyl alcohol, benzyl benzoate, propylene glycol, 1,3-butylglycol, oils, glycerol fatty esters, polyethylene glycol and fatty acid esters of sorbitan.

The formulation of suspension may comprise liquid diluents, for example water, ethanol or propylene glycol, suspending agents such as ethoxylated isosteary alcohols, polyoxyethylene sorbitol esters and poly oxyethylene sorbitan esters, micocrystalline cellulose, aluminum metahydroxide, bentonite, agar or tragacanth.

The formulation of cleansing compositions with surfactant may comprise aliphatic alcohol sulfate, aliphatic alcohol ether sulfate, sulfosucinnate monoester, isothinate, imidazolium derivatives, methyltaurate, sarcocinate, fatty acid amide ether sulfate, alkyl amido betain, aliphatic alcohol, fatty acid glyceride, fatty acid diethanolamide, vegetable oil, lanoline derivatives or ethoxylated glycerol fatty acid ester.

In the pharmaceutical compositions of this invention, the pharmaceutically acceptable carrier may be conventional one for formulation, including lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methyl cellulose, methylhydroxy benzoate, propylhydroxy benzoate, talc, magnesium stearate, and mineral oils, but not limited to. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in *Remington's Pharmaceutical Sciences* (19th ed., 1995), which is incorporated herein by reference.

A pharmaceutical composition of the present invention was developed for the purpose of topical administration to the skin.

A suitable dose of the pharmaceutical composition of the present invention may vary depending on pharmaceutical formulation methods, administration methods, the patient's age, body weight, sex, severity of diseases, diet, administration time, administration route, an excretion rate and sensitivity for a used pharmaceutical composition. A daily dose to topical administration of pharmaceutical composition of the present invention is preferably 0.001-100 ng/cm$^2$ (surface area of skin), more preferably 0.01-10 ng/cm$^2$ and most preferably 0.1-2 ng/cm$^2$.

The pharmaceutical composition of the present invention may be formulated into a unit or multiple dosages form using a pharmaceutically acceptable carrier and/or excipient according to the method easily conducted by a person having ordinary skill in the art to which the present invention pertains. Here, the dosage form is most preferably a solution type containing a nanoliposome.

The composition of the present invention acts on epidermal cells to exhibit efficacies of improving wrinkles and atopic dermatitis diseases. To sum up, the composition of this invention can significantly improve skin conditions and is very safe to the human body.

According to a preferable embodiment of the present invention, the protein having the amino acid sequence of SEQ ID NO: 1 in the composition for improving skin conditions of the present invention may be a thioredoxin-binding fusion protein.

As used herein, the term "fusion protein" refers to a protein in which thioredoxin binds to human bone morphogenetic protein receptor 1a extracellular domain (BMPR1a ECD).

The thioredoxin used in the present invention has a thioredoxin amino acid sequence derived from a microorganism, a human, or an animal, and preferably has a thioredoxin amino acid sequence derived from the microorganism. More preferably, the thioredoxin of the present invention has the amino acid sequence of SEQ ID NO: 3. A nucleic acid encoding thioredoxin of the present invention is most preferably the nucleotide sequence of SEQ ID NO: 4.

According to another embodiment of the present invention, the present invention provides a fusion protein in which thioredoxin binds to the protein having the amino acid sequence of SEQ ID NO: 1 of the present invention.

The thioredoxin comprised in the fusion protein of thioredoxin-human bone morphogenetic protein receptor 1a extracellular domain in the present application has the amino acid sequence of SEQ ID NO:3. The nucleic acid molecule encoding the thioredoxin in the present application has most preferably the nucleotide sequence of SEQ ID NO:4. The nucleic acid molecule encoding the thioredoxin includes nucleotide sequences substantially identical to the above-described nucleotide sequence. The substantial identity means that, when a nucleotide sequence is aligned to maximally match the nucleotide sequence of the present disclosure and the alignment is analyzed using an algorithm commonly used in the art, it has an identity of at least 80%, more preferably at least 90%, and most preferably at least 95%.

According to a preferable embodiment of the present invention, the fusion protein, protein having According to a preferable embodiment of the present invention, the fusion protein that the protein having the amino acid sequence of SEQ ID NO: 1 is fused to the thioredoxin protein has the amino acid sequence of SEQ ID NO: 5.

In another aspect of this invention, there is provided a method for improving skin conditions comprising administering to a subject a composition comprising the protein having the amino acid sequence of SEQ ID NO: 1 as an active ingredient.

Advantageous Effects

Features and advantages of the present invention are summarized as follows:

(i) The present invention provides a composition for improving skin conditions, containing, as an active ingredient, human bone morphogenetic protein receptor 1a extracellular domain (BMPR1a ECD).

(ii) The composition of the present invention exhibits effects of wrinkle improvement and atopic dermatitis improvement.

MODE FOR CARRYING OUT THE INVENTION

Figure 1:
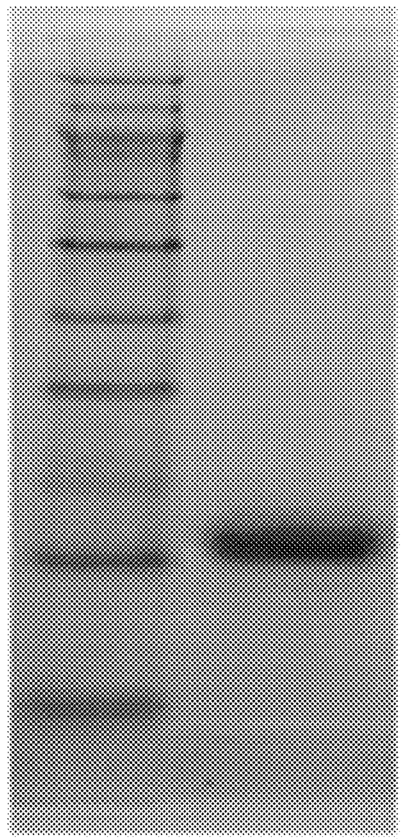
FIG. 1 is an SDS-PAGE gel image confirming human BMPR1a ECD protein, which was transfected in *E. coli*, followed by incubation and purification.

Hereinafter, the present invention will be described in detail with reference to examples. These examples are only for illustrating the present invention more specifically, and it will be apparent to those skilled in the art that the scope of the present invention is not limited by these examples.

EXAMPLES

Example 1

Preparation of Human BMPR1a ECD Expression Vector

Preparation of Thioredoxin-Human BMPR1a ECD Gene

A DNA fragment in which the thioredoxin (TRX) gene derived from *E. coli* was fused to a DNA fragment encoding human bone morphogenetic protein receptor 1a extracellular domain (BMPR1a ECD) was obtained from the synthesis by GeneScript (USA). A linker region composed of 36 amino acids is included between the thioredoxin gene and the BMPR1a ECD gene. The *E. coli* thioredoxin protein is composed of 109 amino acids, and human BMPR1a ECD is composed of 129 amino acids.

Preparation of Expression Vector Containing Thioredoxin-Human BMPR1a ECD Gene

The thioredoxin-human BMPR1a ECD gene and the pET-32a(+) vector (Novagen, USA) were cleaved with MscI and EcoRI and ligated with T4 DNA ligase (NEB, USA), and then transfected in the DH5$\alpha$ strain (BioPrince, USA). The cells were incubated at 37° C. for 15 hours, and then 10 colonies were randomly selected and cultured. Plasmids were obtained by using a plasmid purification kit (Qiagen), and then analyzed on a 1.2% agarose gel through electrophoresis, followed by sequencing, thereby selecting desired plasmids.

Purification of Human BMPR1a ECD Protein and Thioredoxin-Human BMPR1a ECD Protein The expression vector containing the thioredoxin-human BMPR1a ECD gene was transfected in Orgami B(DE3) (Novagen, USA), which is a strain for expression, and then the cells were incubated on a large scale. The Orgami B(DE3) (Novagen, USA) strain transfected with the thioredoxin-human BMPR1a ECD expression vector was incubated in a 50 L incubator at 16° C. to induce expression, and then cell pellets were obtained through centrifugation. The cell pellets were suspended in buffer A (50 mM Tris, 0.5M NaCl, pH 8.0), and disrupted two times for 10 minutes for each time at 800 bar by using a homogenizer. Then, the supernatant was obtained through centrifugation. The sample supernatant was loaded using buffer B (50 mM Tris, 0.5M NaCl, 20 mM imidazole, pH 8.0) and buffer C (50 mM Tris, 0.5 M NaCl, 500 mM imidazole, pH 8.0) to isolate the thioredoxin-human BMPR1a ECD protein, followed by exchange with buffer A and protein concentration using a TFF system. Then, 2,000 units of thrombin per gram of thioredoxin-human BMPR1a ECD protein were put thereinto, followed by standing at 4° C. overnight. Ni-NTA affinity column purification using buffer A and buffer B was conducted. Last, Superdex 100 column chromatography was conducted using buffer A to purify and quantify human BMPR1a ECD protein.

Example 2

Experiment for Verifying Wrinkle Improvement Effect

Treatment of Nude Mice with Protein 4-week-old female nude mice as experimental animals were purchased from DooYeol Biotech (Sungnam, Korea). The experimental animals were bred under conditions of a temperature of 24±2° C. and a humidity of 50±10% in a 12-hr light/12-hr dark cycle. The experimental animals were acclimated for 2 weeks, and then randomly divided into six groups for the experiment. Experiment groups are as shown in Table 1.

TABLE 1

| Group No. | 1 | 2 | 3 | 4 | 5 | 6 |
|---|---|---|---|---|---|---|
| UV radiation | − | + | + | + | + | + |
| Sample | − | − | Ethanol (15 vol %) | 0.01 wt % R.A* | Lipo-some (1%) | Lipo-BMPR1a ECD (13 μg/ml) |
| Volume (μl) | − | − | 300 | 300 | 300 | 300 |

*R.A: retinoic acid, 0.01 w % of retinoic acid dissolved in 15 vol % ethanol

The BMPR1a ECD protein lyophilized at 4° C. was dissolved in 1 L of solution (20 mM $NaH_2PO_4$ [pH 7.0], 1 mM EDTA) to a concentration of 10 μg/ml, and then 10 g of liposome (Soya-SPL 75H, Onetech Co.) was added, followed by stirring for 30 minutes, thereby finally preparing a sample containing 1% liposome and 13 μg/ml of BMPR1a ECD protein. The used liposome contains, as a main component, hydrogenated lecithin derived from soybean. The prepared sample was passed through a high-pressure homogenizer (NanoDeBEE, USA, Model 45-1) equipped with a heat exchanger five times under a pressure of 15,000 psi, thereby preparing a final sample. Most of liposome sizes are 100-200 nm under the above conditions.

Protein treatment group (Group 6), the positive control (Group 4), and Groups 3 and 5 were respectively treated with 300 μl of corresponding samples five times every week. In the case of UV treatment, sample coating was conducted before UV radiation. Each sample was uniformly coated on the full back of a mouse by using Art brush No. 3 (Hwahong, Korea).

UV Radiation to Nude Mice

VLX-3W stimulator (VilberLourmat, MarnelaVallee, France) was used as a UV radiation equipment. UV radiation was conducted three times every week for a total of 11 weeks: 40 mJ/$cm^2$ for $1^{st}$ to $2^{nd}$ weeks; 50 mJ/$cm^2$ for $3^{rd}$ to $4^{th}$ weeks; 60 mJ/$cm^2$ for $5^{th\ to}$ $9^{th}$ weeks; and 70 mJ/$cm^2$ for $10^{th}$ to $11^{th}$ weeks.

Winkle Improvement Effect of Lipo-BMPR1a ECD

Figure 2:
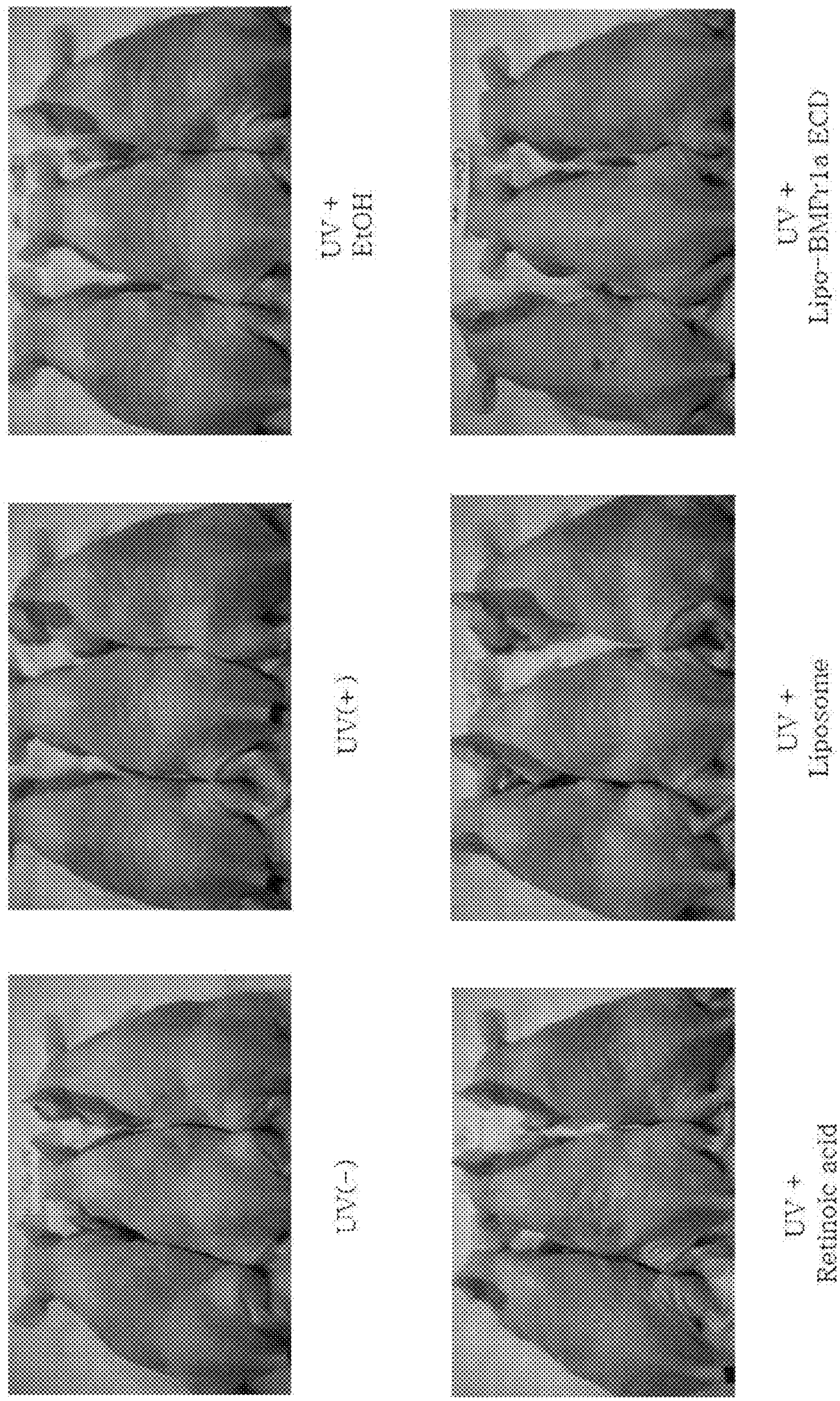
FIG. 2 verifies a wrinkle improvement effect at the protein coated region after a nude mouse having wrinkles induced through UV radiation was coated with Lipo-BMPR1a ECD for 11 weeks.

The back of each experimental animal was photographed every week, and a person who did not participate in the experiment observed skin conditions based on photographs, to evaluate the wrinkle improvement effects expressed as wrinkle scores of 10 grades in consideration of overall items of the number, thickness, and depth of coarse wrinkles transversely induced by UV radiation (FIGS. 1-2). As the result of integration of the evaluations on respective items through observation by the naked eye, it was verified that the skin wrinkles were improved by about 75% in the group coated with Lipo-BMPR1a (liposome-BMPR1a) ECD than in the group treated with only UV.

Example 3

Experiment for Verifying Atopic Dermatitis Improvement Effect

Experimental Animals

NC/Ng mice (male, 4 weeks old, Central Lab. Animal Inc. Korea) were acclimated for 2 weeks under conditions of a temperature of 24±2° C. and a humidity of 50±10% in a 12-hr light/12-hr dark cycle, for the experiment. The mice acclimated for 2 weeks were weighed, and divided into five groups as shown in Table 2 below.

TABLE 2

| | Group No. | | | | |
|---|---|---|---|---|---|
| | 1 | 2 | 3 | 4 | 5 |
| TNCB | + | + | + | + | + |
| Sample | − | DMSA (5 vol %) | FK506 (0.03 wt %) | Liposome (1%) | Lipo-BMPR1a ECD(13 μg/ml) |
| Sample volume (μl) | − | 100 | 100 | 300 | 300 |

TNCB (1,3,5-trinitrochlorobenzene, Sigma, USA): atopy inducer
FK506: Positive control group, T cell immunosupressor Atopy Induction and Sample Coating For the induction of atopic dermatitis diseases, to begin with, the fur on the back of each experimental animal was removed by using a depilatory. Then, the back of each experimental animal was coated with 4% SDS solution, following by drying, and then coated with 150 μl of 5% TNCB (dissolved in acetone:ethanol=1:4). After five days, 150 μl of 1% TNCB (dissolved in olive oil) was coated thereon a total of five times at intervals of one week to induce atopy. After the atopy was induced by the TNCB coating for five weeks, FK506 and Lipo-BMPR1a ECD were coated five times every week for 10 weeks, respectively.

Atopic Dermatitis Improvement Effect of Lipo-BMPR1a ECD

Figure 3:
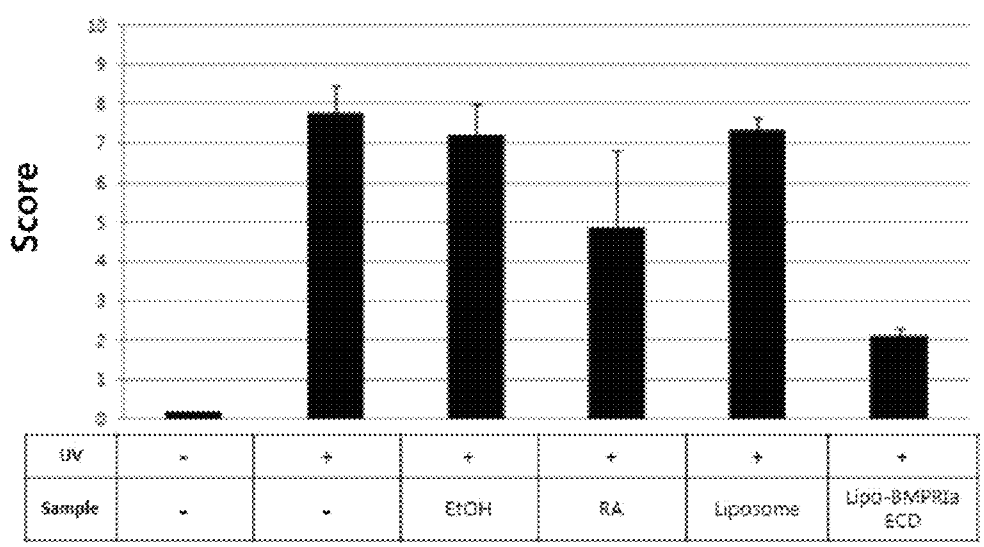
FIG. 3 is a graph evaluating a wrinkle improvement effect expressed as a score based on a photograph of the Lipo-BMPR1a ECD coated region.
Figure 4:
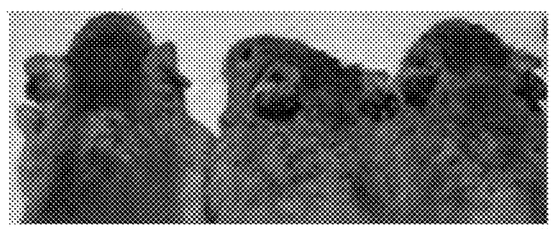
FIG. 4 verifies a wrinkle improvement effect at the protein coated region after the mouse having atopy induced through TNCB coating was coated with Lipo-BMPR1a ECD for 10 weeks.
Figure 4:
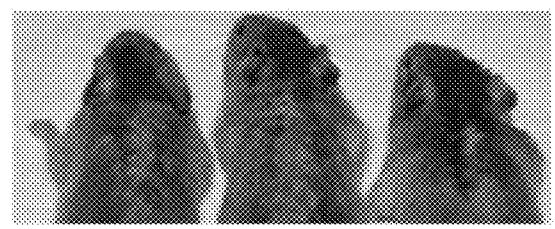
Figure 4:
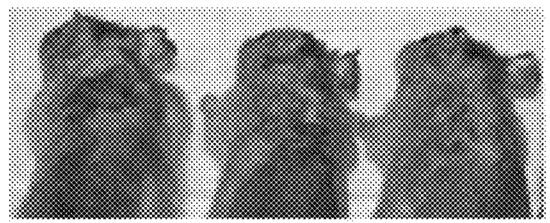
Figure 4:
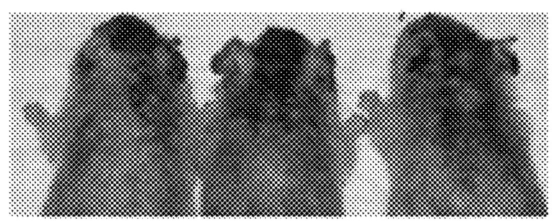
Figure 4:
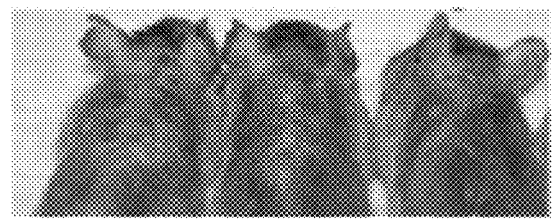
Figure 5:
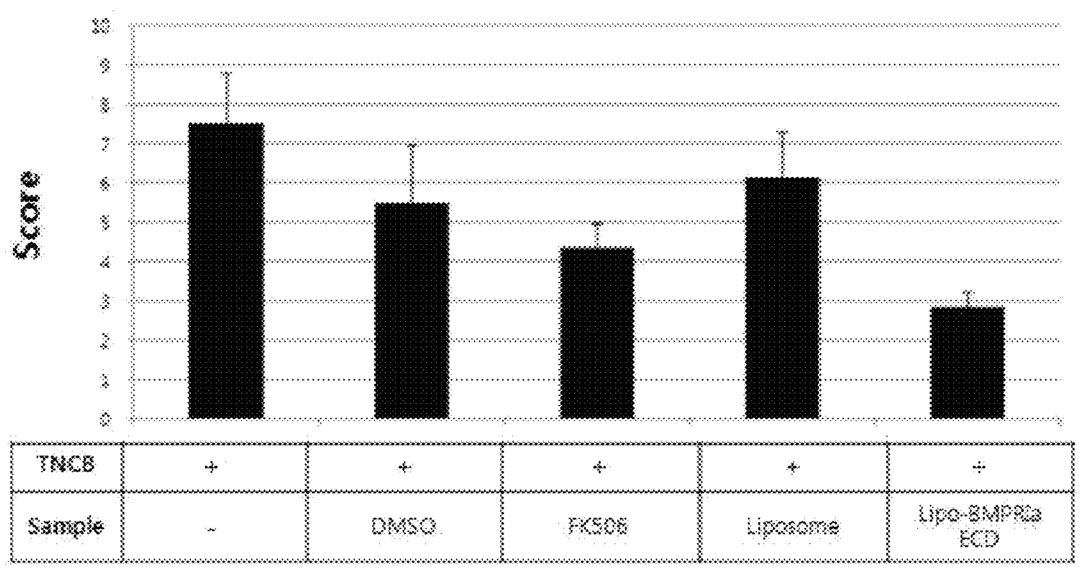
FIG. 5 is a graph evaluating an atopic dermatitis improvement effect expressed as a score based on a photograph of the Lipo-BMPR1a ECD coated region.
Figure 6:
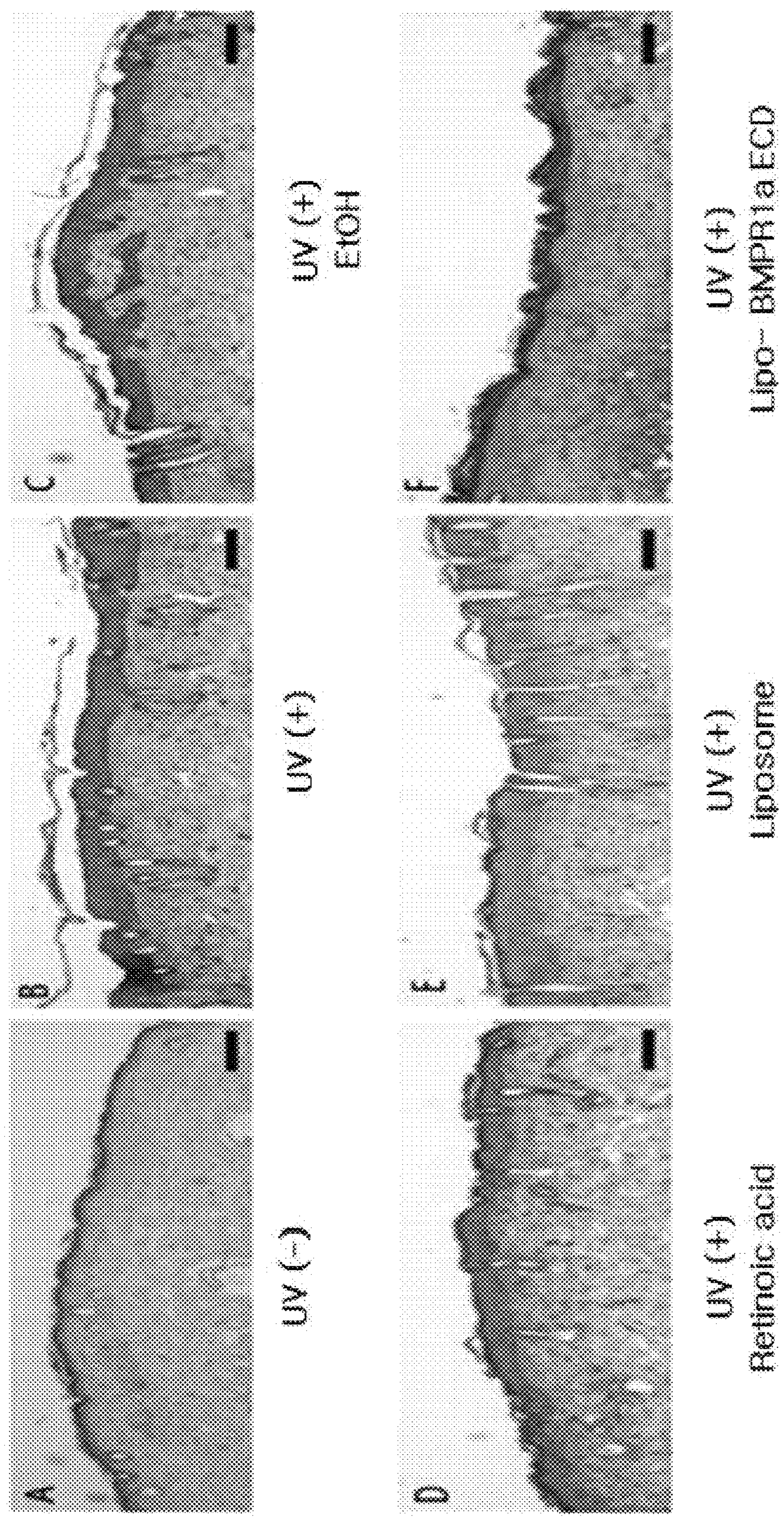
FIG. 6 verifies epidermal thickness due to Lipo-BMPR1a ECD coating by Hematoxylin & Eosin staining.
Figure 7:
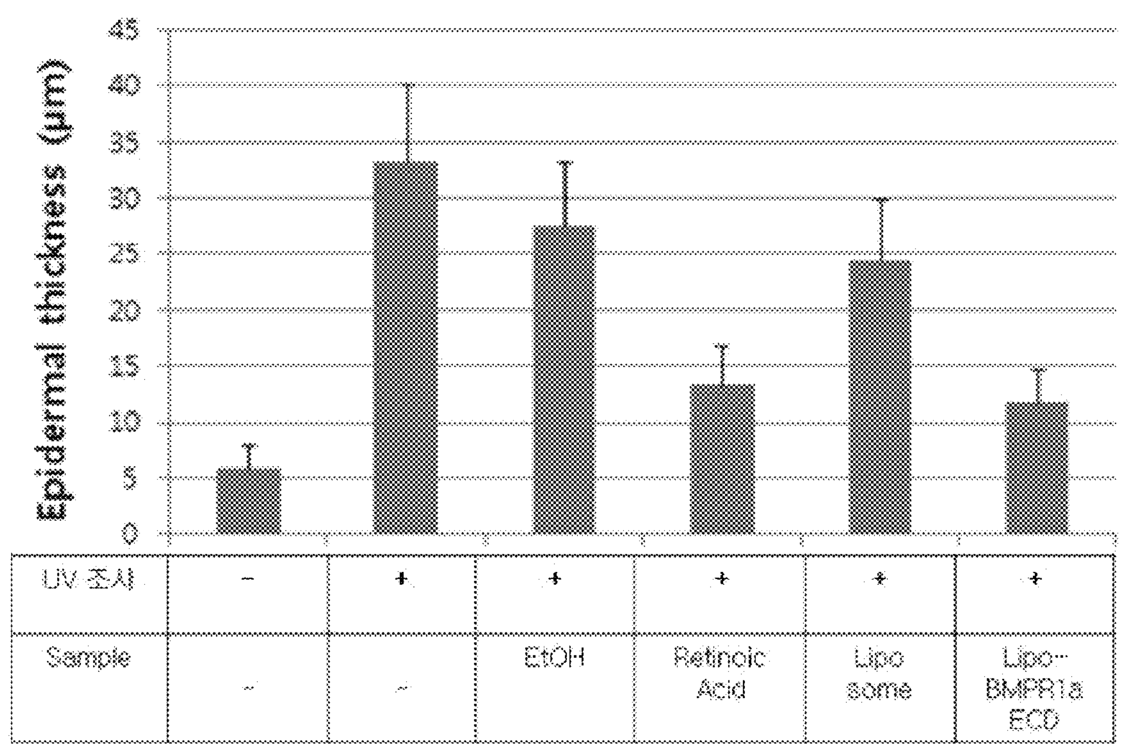
FIG. 7 is a graph showing measurement results of epidermal thickness due to Lipo-BMPR1a ECD coating.
Figure 8:
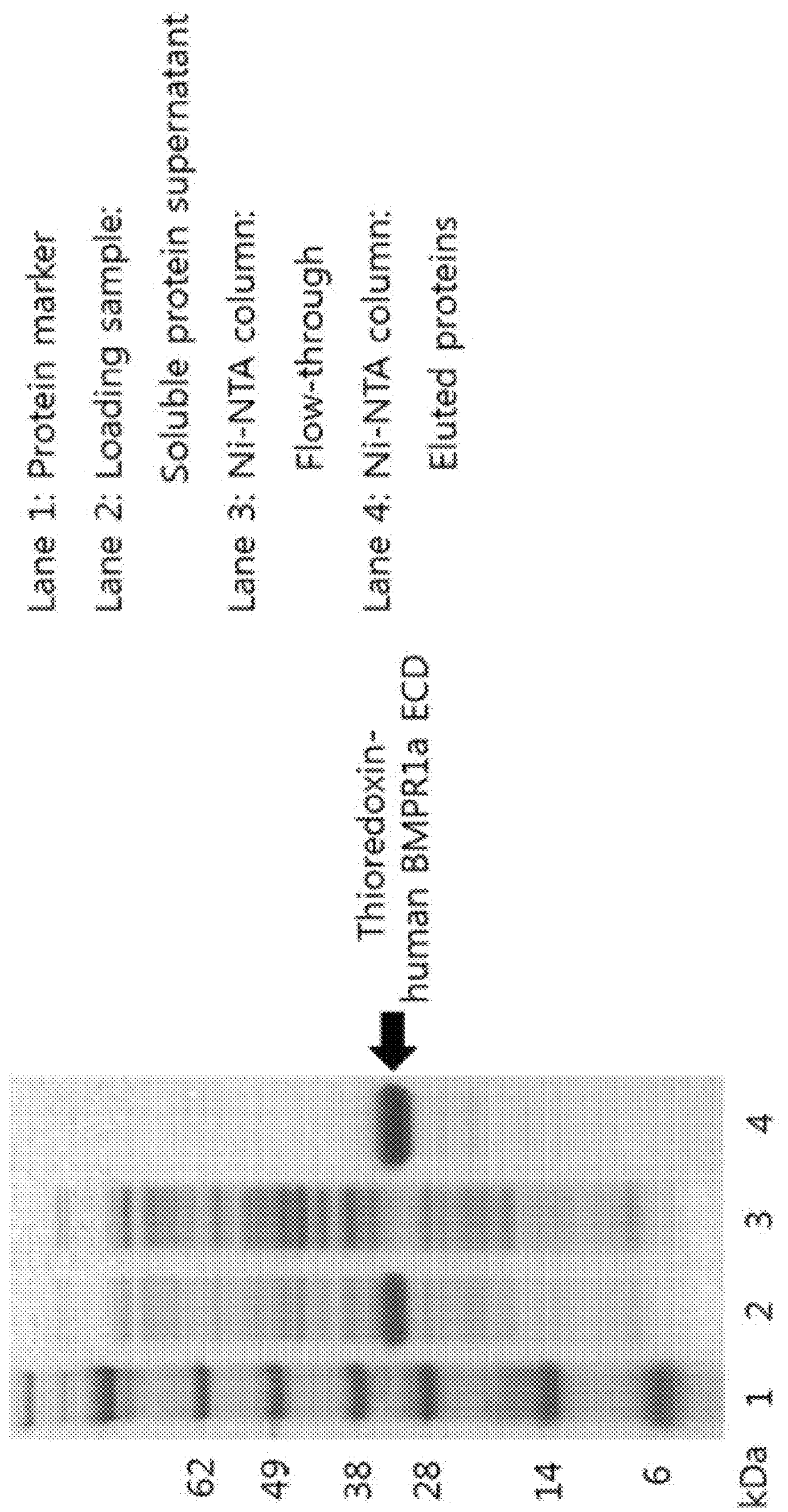
FIG. 8 is an SDS-PAGE gel image confirming thioredoxin-BMPR1a ECD fusion protein, which was transfected in *E. coli*, followed by incubation and purification.

The back of each experimental animal was photographed every week, and a person who did not participate in the experiment observed skin conditions based on photographs, to evaluate the atopic symptoms expressed as scores of 10 grades in consideration of four items of erythema, edema, abrasion, and dryness (FIGS. 3-4). As the result of integration of the evaluations on respective items through observation by the naked eye, it was verified that the atopic dermatitis disease was improved by about 60% in the group coated with Lipo-BMPR1a ECD than in the group treated with only TNCB.

Example 4

Experiment for Measuring Epidermal Thickness

Experimental Animals

SKH-1 nude mice (female, 4 weeks old, DooYeol Biotech, Korea) were acclimated for about 2 weeks under conditions of a temperature of 24±2° C. and a humidity of 50±10% in a 12-hr light/12-hr dark cycle, and then divided into six groups for the experiment.

TABLE 3

| Group No. | 1 | 2 | 3 | 4 | 5 | 6 |
|---|---|---|---|---|---|---|
| UV radiation | − | + | + | + | + | + |
| Sample | − | − | EtOH (15%) | Retinoic acid (0.01%) | Lipo-some (1%) | Lipo-BMPR1a ECD (1 μM) |
| Sample volume (μl) | − | − | 300 | 300 | 300 | 300 |

Sample Coating

The protein group and control group were respectively treated with 300 of corresponding samples every week five times. For UV treatment, the back of each mouse was uniformly coated with the previously prepared sample one hour before UV radiation by using Art brush No. 3 (Hwa-hong, Incheon Korea).

UV Radiation to Nude Mice

VLX-3W stimulator (Vilber Lourmat, Marne la Vallee, France) was used for a UV radiation equipment. UV radiation was conducted three times every week for a total of 11 weeks: 40 mJ/cm$^2$ for 1$^{st}$ to 2$^{nd}$ weeks; 50 mJ/cm$^2$ for 3$^{rd}$ to 4$^{th}$ weeks; 60 mJ/cm$^2$ for 5$^{th}$ to 9$^{th}$ weeks; and 70 mJ/cm$^2$ for 10$^{th}$ to 11$^{th}$ weeks.

Mouse Skin Staining

Upon completion of the three-month experiments on the six groups, Hematoxylin & Eosin staining was conducted according to the method known in the art.

Suppression of Lipo-BMPR1a ECD on Epidermal Thickness Increase

As the result of Hematoxylin & Eosin staining, the thickening of skin epidermis due to UV radiation was significantly suppressed in the group treated with Lipo-BMPR1a ECD, and the effect thereof was at least equal as compared with the group treated with retinoic acid.

Example 5

Measurement on Wrinkle Improvement Effect of Thioredoxin-Human BMPR1a ECD

Experimental Animals

SKH-1 nude mice (female, 4 weeks old, DooYeol Bio-tech, Korea) were acclimated for about 2 weeks under conditions of a temperature of 24±2° C. and a humidity of 50±10% in a 12-hr light/12-hr dark cycle, and then divided into six groups for the experiment.

TABLE 4

| | Group No. | | | | |
|---|---|---|---|---|---|
| | 1 | 2 | 3 | 4 | 5 |
| UV radiation | − | + | + | + | + |
| Sample | − | − | Retinoic acid (0.01%) | Lipo-BMPR1a ECD(1 μM) | Lipo-thioredoxin BMPR1a ECD (1 μM) |
| Sample volume (μl) | − | − | 300 | 300 | 300 |

Sample Coating

The protein group and control group were respectively treated with 300 of corresponding samples every week five times. For UV treatment, the back of each mouse was uniformly coated with the previously prepared sample one hour before UV radiation by using Art brush No. 3 (Hwa-hong, Incheon Korea).

UV Radiation to Nude Mice

VLX-3W stimulator(Vilber Lourmat, Marne la Vallee, France) was used for a UV radiation equipment. UV radiation was conducted three times every week for a total of 11 weeks: 40 mJ/cm$^2$ for 1$^{st}$ to 2$^{nd}$ weeks; 50 mJ/cm$^2$ for 3$^{rd}$ to 4$^{th}$ weeks; 60 mJ/cm$^2$ for 5$^{th}$ to 9$^{th}$ weeks; and 70 mJ/cm$^2$ for 10$^{th}$ to 11$^{th}$ weeks.

Winkle Improvement Effect of Lipo-Thioredoxin-BMPR1a ECD

Figure 9:
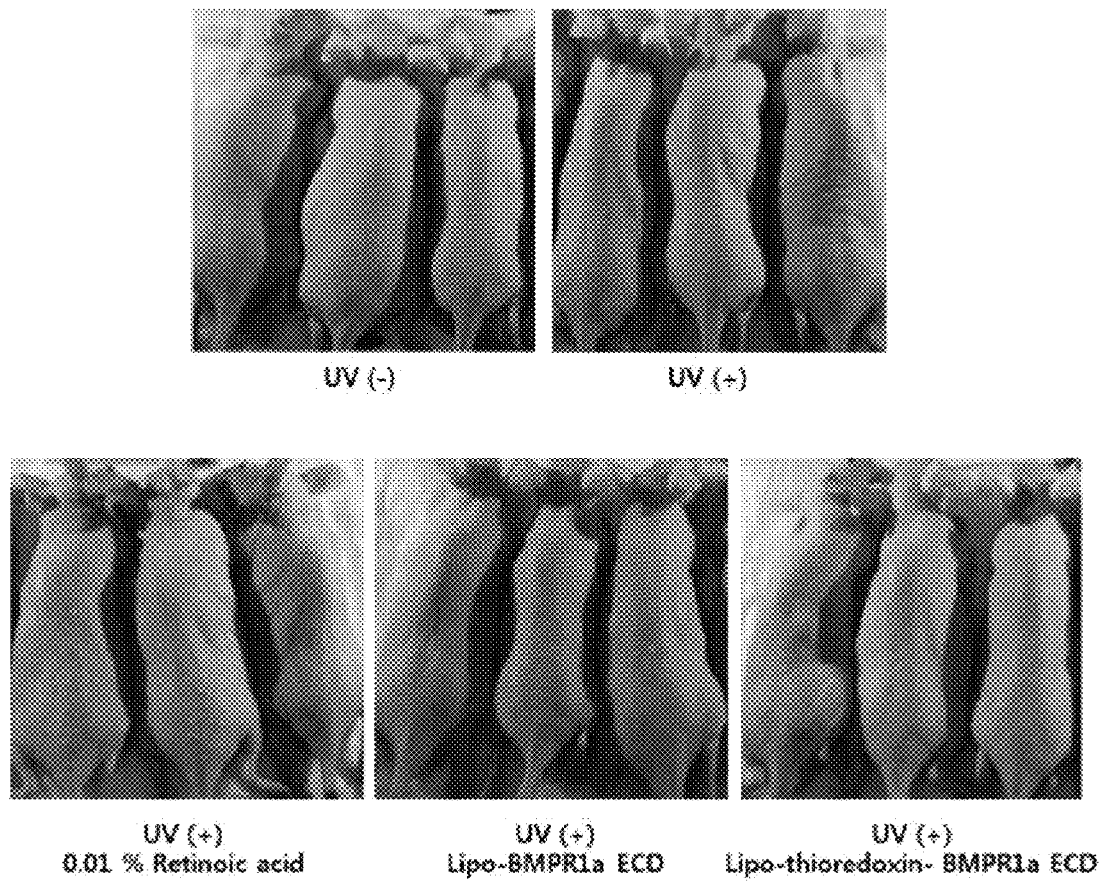
FIG. 9 is a graph evaluating a wrinkle improvement effect when thioredoxin-BMPR1a ECD fusion protein was coated on a nude mouse.
Figure 10:
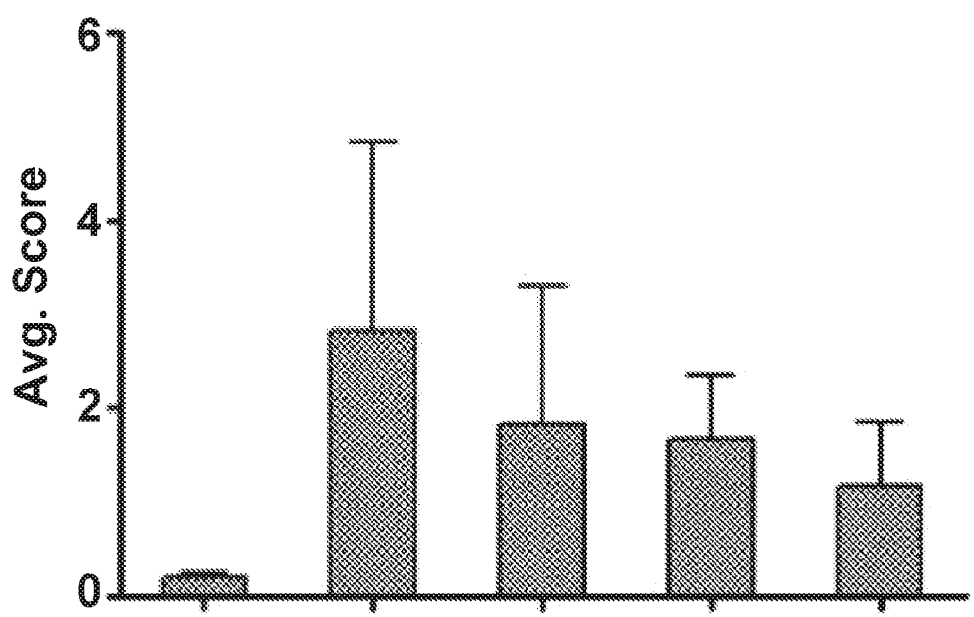
FIG. 10 is a graph evaluating a wrinkle improvement effect expressed as a score based on a photograph of the thioredoxin-BMPR1a ECD fusion protein coated region.

The back of each experimental animal was photographed every week, and a person who did not participate in the experiment observed skin conditions based on photographs, to evaluate the wrinkle improvement effects expressed as wrinkle scores of 10 grades in overall consideration of the number, thickness, and depth of coarse wrinkles that were transversely induced by UV radiation (FIGS. 9-10). As the result of integration of the evaluations on respective items through observation by the naked eye, it was verified that skin wrinkles were improved by about 38% in the group coated with retinoic acid, about 42% in the group treated with Lipo-BMPR1a ECD, and about 59% in the group treated with Lipo-thioredoxin-BMPR1a ECD.

The invention claimed is:

1. A method for improving a skin condition selected from the group consisting of wrinkles and dermatitis in a subject, the method comprising:

topically administering to the subject a composition consisting essentially of an extracellular domain of BMPR1a, wherein the extracellular domain comprises the amino acid sequence of SEQ ID NO: 1, and wherein the extracellular domain is a BMP antagonist.

2. The method of claim 1, wherein the composition is a composition for topical administration to skin.

3. The method of claim 1, wherein a protein having the amino acid sequence of SEQ ID NO: 1 is encapsulated in a liposome.

4. The method of claim 3, wherein the liposome is a nanoliposome.

5. The method of claim 4, wherein the nanoliposome contains lecithin as a constituent component.

6. The method of claim 1, wherein the method suppresses the thickening of skin epidermis on the subject.

7. The method of claim 1, wherein the skin condition is dermatitis.

8. The method of claim 1, wherein the composition is a cosmetic composition or a pharmaceutical composition.

9. The method of claim 1, wherein the extracellular domain is fused to a thioredoxin.

10. The method of claim 7, wherein the dermatitis is atopic dermatitis.

11. The method of claim 1, wherein the skin condition is wrinkles.

* * * * *

SEQUENCE LISTING

```
<160> NUMBER OF SEQ ID NOS: 6

<210> SEQ ID NO 1
<211> LENGTH: 129
<212> TYPE: PRT
<213> ORGANISM: Homo sapiens

<400> SEQUENCE: 1

Gln Asn Leu Asp Ser Met Leu His Gly Thr Gly Met Lys Ser Asp Ser
1               5                   10                  15

Asp Gln Lys Lys Ser Glu Asn Gly Val Thr Leu Ala Pro Glu Asp Thr
            20                  25                  30

Leu Pro Phe Leu Lys Cys Tyr Cys Ser Gly His Cys Pro Asp Asp Ala
```

```
        35                  40                  45

Ile Asn Asn Thr Cys Ile Thr Asn Gly His Cys Phe Ala Ile Ile Glu
    50                  55                  60

Glu Asp Asp Gln Gly Glu Thr Thr Leu Ala Ser Gly Cys Met Lys Tyr
65                  70                  75                  80

Glu Gly Ser Asp Phe Gln Cys Lys Asp Ser Pro Lys Ala Gln Leu Arg
                85                  90                  95

Arg Thr Ile Glu Cys Cys Arg Thr Asn Leu Cys Asn Gln Tyr Leu Gln
            100                 105                 110

Pro Thr Leu Pro Pro Val Val Ile Gly Pro Phe Phe Asp Gly Ser Ile
        115                 120                 125

Arg


<210> SEQ ID NO 2
<211> LENGTH: 387
<212> TYPE: DNA
<213> ORGANISM: Homo sapiens

<400> SEQUENCE: 2

cagaatctgg atagtatgct tcatggcact gggatgaaat cagactccga ccagaaaaag     60

tcagaaaatg gagtaacctt agcaccagag gataccttgc ctttttaaa gtgctattgc    120

tcagggcact gtccagatga tgctattaat aacacatgca taactaatgg acattgcttt    180

gccatcatag aagaagatga ccagggagaa accacattag cttcagggtg tatgaaatat    240

gaaggatctg attttcagtg caaagattct ccaaaagccc agctacgccg gacaatagaa    300

tgttgtcgga ccaatttatg taaccagtat ttgcaaccca cactgccccc tgttgtcata    360

ggtccgtttt ttgatggcag cattcga                                        387


<210> SEQ ID NO 3
<211> LENGTH: 109
<212> TYPE: PRT
<213> ORGANISM: Escherichia coli

<400> SEQUENCE: 3

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala
            100                 105


<210> SEQ ID NO 4
<211> LENGTH: 327
<212> TYPE: DNA
<213> ORGANISM: Escherichia coli

<400> SEQUENCE: 4

atgagcgata aaattattca cctgactgac gacagttttg acacggatgt actcaaagcg     60
```

```
gacggggcga tcctcgtcga tttctgggca gagtggtgcg gtccgtgcaa aatgatcgcc    120

ccgattctgg atgaaatcgc tgacgaatat cagggcaaac tgaccgttgc aaaactgaac    180

atcgatcaaa accctggcac tgcgccgaaa tatggcatcc gtggtatccc gactctgctg    240

ctgttcaaaa acggtgaagt ggcggcaacc aaagtgggtg cactgtctaa aggtcagttg    300

aaagagttcc tcgacgctaa cctggcc                                        327


<210> SEQ ID NO 5
<211> LENGTH: 274
<212> TYPE: PRT
<213> ORGANISM: Homo sapiens

<400> SEQUENCE: 5

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Met His His His His His His Ser Ser Gly Gly Ser Ser
        115                 120                 125

Thr Ser Leu Tyr Lys Lys Ala Gly Ser Leu Val Pro Arg Gly Ser Gly
    130                 135                 140

Thr Gln Asn Leu Asp Ser Met Leu His Gly Thr Gly Met Lys Ser Asp
145                 150                 155                 160

Ser Asp Gln Lys Lys Ser Glu Asn Gly Val Thr Leu Ala Pro Glu Asp
                165                 170                 175

Thr Leu Pro Phe Leu Lys Cys Tyr Cys Ser Gly His Cys Pro Asp Asp
            180                 185                 190

Ala Ile Asn Asn Thr Cys Ile Thr Asn Gly His Cys Phe Ala Ile Ile
        195                 200                 205

Glu Glu Asp Asp Gln Gly Glu Thr Thr Leu Ala Ser Gly Cys Met Lys
    210                 215                 220

Tyr Glu Gly Ser Asp Phe Gln Cys Lys Asp Ser Pro Lys Ala Gln Leu
225                 230                 235                 240

Arg Arg Thr Ile Glu Cys Cys Arg Thr Asn Leu Cys Asn Gln Tyr Leu
                245                 250                 255

Gln Pro Thr Leu Pro Pro Val Val Ile Gly Pro Phe Phe Asp Gly Ser
            260                 265                 270

Ile Arg


<210> SEQ ID NO 6
<211> LENGTH: 822
<212> TYPE: DNA
<213> ORGANISM: Homo sapiens

<400> SEQUENCE: 6
```

-continued

```
atgagcgata aaattattca cctgactgac gacagttttg acacggatgt actcaaagcg    60
gacggggcga tcctcgtcga tttctgggca gagtggtgcg gtccgtgcaa aatgatcgcc   120
ccgattctgg atgaaatcgc tgacgaatat cagggcaaac tgaccgttgc aaaactgaac   180
atcgatcaaa accctggcac tgcgccgaaa tatggcatcc gtggtatccc gactctgctg   240
ctgttcaaaa acggtgaagt ggcggcaacc aaagtgggtg cactgtctaa aggtcagttg   300
aaagagttcc tcgacgctaa cctggccggt tctggttctg gccacatgca ccatcatcat   360
catcattctt ctggtggatc atcaacaagt ttgtacaaaa aagcaggctc tctggtgcca   420
cgcggttctg gtacccagaa tctggatagt atgcttcatg gcactgggat gaaatcagac   480
tccgaccaga aaaagtcaga aaatggagta accttagcac cagaggatac cttgcctttt   540
ttaaagtgct attgctcagg gcactgtcca gatgatgcta ttaataacac atgcataact   600
aatggacatt gctttgccat catagaagaa gatgaccagg gagaaaccac attagcttca   660
gggtgtatga aatatgaagg atctgatttt cagtgcaaag attctccaaa agcccagcta   720
cgccggacaa tagaatgttg tcggaccaat ttatgtaacc agtatttgca acccacactg   780
ccccctgttg tcataggtcc gttttttgat ggcagcattc ga                      822
```